(12) United States Patent
Magnusson et al.

(10) Patent No.: US 9,254,226 B2
(45) Date of Patent: Feb. 9, 2016

(54) AUTOMATIC WELDING FILTER WITH TUNABLE SPECTRAL TRANSMISSION

(71) Applicant: 3M INNOVATIVE PROPERTIES COMPANY, St. Paul, MN (US)

(72) Inventors: Kristina M. Magnusson, Djurmo (SE); Kenneth Jarefors, Borlange (SE)

(73) Assignee: 3M Innovative Properties Company, St. Paul, MN (US)

( * ) Notice: Subject to any disclaimer, the term of this patent is extended or adjusted under 35 U.S.C. 154(b) by 40 days.

(21) Appl. No.: 14/372,087

(22) PCT Filed: Jan. 15, 2013

(86) PCT No.: PCT/US2013/021512
§ 371 (c)(1),
(2) Date: Jul. 14, 2014

(87) PCT Pub. No.: WO2013/115970
PCT Pub. Date: Aug. 8, 2013

(65) Prior Publication Data
US 2015/0001378 A1  Jan. 1, 2015

(30) Foreign Application Priority Data

Jan. 25, 2012 (GB) .................................. 1201164.9

(51) Int. Cl.
*G02F 1/00* (2006.01)
*A61F 9/06* (2006.01)
(Continued)

(52) U.S. Cl.
CPC .............. *A61F 9/067* (2013.01); *G02F 1/1347* (2013.01); *G02F 1/13338* (2013.01);
(Continued)

(58) Field of Classification Search
CPC .............. A61F 9/067; G02F 1/133512; G02F 1/133528; G02F 1/1347
See application file for complete search history.

(56) References Cited

U.S. PATENT DOCUMENTS

| 3,112,490 A | 12/1963 | Malcom, Jr. |
| 4,240,709 A * | 12/1980 | Hornell .................. A61F 9/067 349/104 |

(Continued)

FOREIGN PATENT DOCUMENTS

| CN | 2011-23869 | 10/2008 |
| EP | 0706674 | 4/1996 |

(Continued)

OTHER PUBLICATIONS

Kim, "Visible Light Emissions During Gas Tungsten Arc Welding and Its Application to Weld Image Improvement", Welding Research Supplement, Dec. 1987, pp. 369s-377s.

(Continued)

*Primary Examiner* — Tony Ko
(74) *Attorney, Agent, or Firm* — Melanie G. Gover

(57) ABSTRACT

The present invention relates to an automatic welding filter that changes from a light transmission state to a dark transmission state in response to incident welding light and includes a color-tunable filter whose spectral transmittance can be varied to optimize the visual appearance of a welding task. The color-tunable filter comprises at least one low twist liquid crystal cell disposed between polarization filters having substantially parallel polarization directions. The user is able to adjust the color of the automatic welding filter in the dark transmission state, independently of the shade, in response to a user selected color signal which alters the birefringence properties of the low twist liquid crystal cell.

20 Claims, 3 Drawing Sheets

(51) Int. Cl.
- *G02F 1/1335* (2006.01)
- *G02F 1/1347* (2006.01)
- *G02F 1/1333* (2006.01)
- *G02F 1/23* (2006.01)
- G02F 1/139 (2006.01)
- G02F 1/133 (2006.01)

(52) U.S. Cl.
CPC ... *G02F 1/133512* (2013.01); *G02F 1/133528* (2013.01); *G02F 1/23* (2013.01); *A61F 9/065* (2013.01); *G02F 1/13318* (2013.01); *G02F 2001/1398* (2013.01); *G02F 2001/133531* (2013.01); *G02F 2203/055* (2013.01)

(56) References Cited

U.S. PATENT DOCUMENTS

| | | | |
|---|---|---|---|
| 4,728,173 | A | 3/1988 | Toth |
| 4,867,536 | A | 9/1989 | Pidsosny |
| 5,208,688 | A | 5/1993 | Fergason |
| 5,519,522 | A | 5/1996 | Fergason |
| 5,642,214 | A | 6/1997 | Ishii |
| 5,689,317 | A | 11/1997 | Miller |
| 5,857,215 | A * | 1/1999 | Fergason ............ A61F 9/06 2/412 |
| 6,273,571 | B1 | 8/2001 | Sharp |
| 7,477,330 | B2 * | 1/2009 | Magnusson ....... G02F 1/133528 2/8.8 |
| 2001/0017681 | A1 | 8/2001 | Hornell |
| 2007/0056073 | A1 | 3/2007 | Martin |

FOREIGN PATENT DOCUMENTS

| | | |
|---|---|---|
| EP | 1935386 | 6/2008 |
| JP | 2000-267127 | 9/2000 |
| JP | 2005-115208 | 4/2005 |
| WO | WO 91/06888 | 5/1991 |
| WO | WO 95/29428 | 11/1995 |
| WO | WO 97/15256 | 5/1997 |
| WO | WO 01/81037 | 11/2001 |
| WO | WO 02/02267 | 1/2002 |
| WO | WO 2007/047264 | 4/2007 |

OTHER PUBLICATIONS

Weglowski, "Investigation on the electric arc light emission in TIG welding", International Journal of Computational Materials Science and Surface Engineering, 2007, vol. 1, No. 6, pp. 734-749.

International Search Report for PCT International Application No. PCT/US2013/021512 mailed on Jun. 26, 2013, 3 pages.

European Application No. 13743198 Search Report dated Jul. 28, 2015.

Holland, C.E., New Technologies Improve Passive LCDs and Expand Design Flexibility, Nov. 4, 1997, pp. 150-159, XP01254377, DOI: 10.1109/WESCON.1997.632331, ISBN: 978-0-7803-4303-0.

* cited by examiner

AUTOMATIC WELDING FILTER WITH TUNABLE SPECTRAL TRANSMISSION

TECHNICAL FIELD OF THE INVENTION

The present invention relates to an automatic welding filter. In particular, the present invention relates to an automatic welding filter that changes from a light transmission state to a dark transmission state in response to incident welding light and includes a colour-tunable filter whose spectral transmittance can be varied to optimise the visual appearance of a welding task.

BACKGROUND

Automatic welding filters are well known, and generally consist of a switchable filter being located on, or as part of, personal protective equipment (e.g., headwear or eyewear). The switchable filter is able to automatically switch from a light transmission state to a dark transmission state in response to activation by welding light. This is generally achieved by using a sensor located on, or as part of, personal protective equipment that detects the start of a welding arc and generates a corresponding control voltage which, when applied to the switchable filter, causes it to change from a light transmission state to a dark transmission state. Activation of the switchable filter can also be controlled by transmitting activation signals along a communication channel between a welding torch and the automatic welding filter, which is controlled by a corresponding communication unit, see WO2007/047264 (Garbergs, et al.). This technique ensures that the welding tool is not activated before the switchable filter has reached its dark transmission state.

U.S. Pat. No. 4,240,709 (Hornell) describes that a switchable filter can be formed by sandwiching a single twisted nematic liquid crystal cell between a pair of mutually crossed polarisers; however, the majority of commercial products now utilise a switchable filter formed by sandwiching two twisted nematic liquid crystal cells between three crossed polarisers. The liquid crystal molecules are able to orientate when a voltage is applied across the liquid crystal cells, under the control of an electronic module. The switchable filter is then automatically darkened by the electronic module, upon detection of incident welding light that falls on a photodetector. Prior art automatic welding filters also include an interference filter which attenuates the harmful IR and UV wavelength components of the welding light, and a third liquid crystal cell can sometimes be included (usually a guest-host type liquid crystal cell) which provides a "fail-safe" intermediate transmission state in the case of failure of the electronic module. WO95/29428 (Hornell, et al.) discloses such a prior art automatic welding filter.

The invention described in WO95/29428 also addresses the problem that, in the dark transmission state, the switchable filter is darkened unevenly due to the fact that the filter effect is heavily dependent upon the angle of incidence of the welding light. WO95/29428 proposes a switchable filter including low twisted nematic liquid crystal cells, where the twist angle differs from the conventional 90 degrees, and is less than 85 degrees. This approach gives significant improvements in terms of homogeneity in the dark transmission state of the switchable filter.

The use of such an automatic welding filter can greatly increase the accuracy of electrode placement, giving higher quality welds. Productivity is also increased as the need for grinding and rework is correspondingly reduced. However, with existing automatic welding filters, the emission spectrum of welding light varies depending on the welding method and materials used, and this can sometimes make viewing the welding task more difficult in the dark transmission state and which can otherwise lead to a reduction in efficiency and weld quality.

SUMMARY OF THE INVENTION

The present invention aims to address these issues by providing an automatic welding filter, comprising: a switchable filter that changes from a light transmission state to a dark transmission state in response to an activation signal; a colour-tunable filter, being in optical alignment with the switchable filter, whose spectral transmittance is adapted to vary in response to a user-selected colour signal; and an electronic control unit for receiving and controlling the signals.

An advantage of using a colour-tunable filter whose spectral transmittance can be varied in response to a user-selected colour signal is that the user is able to adjust the colour of the automatic welding filter in the dark transmission state, independently of the shade, to improve the visibility and optimise the visual appearance of a wide variety of welding tasks. Preferably the colour-tunable filter comprises at least one low twist liquid crystal cell disposed between polarisation filters having substantially parallel polarisation directions.

Further the user-selected colour signal alters the birefringence properties of the low twist liquid crystal cell.

The twist angle of the low twist liquid crystal cell may be between 0 degrees and 60 degrees.

Preferably the twist angle of the low twist liquid crystal cell is between 30 degrees and 50 degrees.

Further the polarisation filters having substantially parallel polarisation directions are aligned at an angle between 0 degrees and 15 degrees.

The switchable filter may comprise first and second twisted nematic liquid crystal cells; and wherein the first liquid crystal cell is disposed between first and second polarization filters, and wherein the second liquid crystal cell is disposed between second and third polarisation filters, the polarisation filters having substantially orthogonal polarization directions; and a band pass filter.

Preferably the twist angles of the first and second liquid crystal cells are between 20 degrees and 85 degrees.

Further the bass pass filter attenuates the IR and UV wavelength components. In the event of failure of the electronic control unit the colour-tunable filter may default to a fail-safe mode of operation by providing an intermediate transmission state.

Preferably the light transmission state corresponds to any of welding shades 2 to 4 and the dark transmission state corresponds to any of welding shades 7 to 14.

Further the intermediate transmission state corresponds to any of welding shades 5 to 8.

The user-selected colour signal may be independent of the transmission state of the switchable filter.

Preferably the user-selected colour signal is adapted to vary in a continuous manner or by selecting a plurality of pre-defined user settings.

Further the spectral transmittance of the colour-tunable filter can be varied in the visible light range of 380 nm to 780 nm.

The present invention also provides a welding shield, comprising a protective shell with the automatic welding filter as described above disposed therein; and at least one sensor connected to the electronic control unit to detect incident light, the electronic control unit causes a voltage to be applied to the switchable filter in response to the activation signal which is indicative of the presence of incident light.

Preferably the automatic welding filter is replaceable.

The present invention also provides a method of filtering high intensity welding light, comprising the steps of: directing the light through a band pass filter that attenuates the IR and UV wavelength components; directing the light through a switchable filter that automatically changes from a light transmission state to a dark transmission state in response to an activation signal; and directing the light through a colour-tunable filter whose spectral transmittance can be varied in response to a user-selected colour signal.

Further the switchable filter and colour-tunable filters are liquid crystal cells.

Preferably the present invention further comprising the steps of: detecting the presence of high intensity welding light using at least one sensor connected to an electronic control unit; and applying a voltage to the switchable filter in response to the sensed activation signal.

BRIEF DESCRIPTION OF THE DRAWINGS

The present invention will now be described by way of example only, and with reference to the accompanying drawings, in which.

DETAILED DESCRIPTION OF THE PREFERRED EMBODIMENTS

The present invention has adopted the approach that it is beneficial for the user to be able to adjust the colour of the automatic welding filter in the dark transmission state, independently of the shade, to improve the visibility of different welding tasks. The emission spectrum obtained from the welding arc varies depending on the welding method employed, the materials, and the shielding gas and current used. Equally, light scattered from the welding fumes will also affect the visual appearance of the task. This can otherwise make viewing the welding task much more difficult in the dark transmission state which can lead to a reduction in efficiency and weld quality. Advantageously, by providing a colour-tunable filter which additionally returns to a fail-safe condition in the event of failure of the electronic module means that an additional guest-host liquid crystal cell is no longer required.

Figure 1:
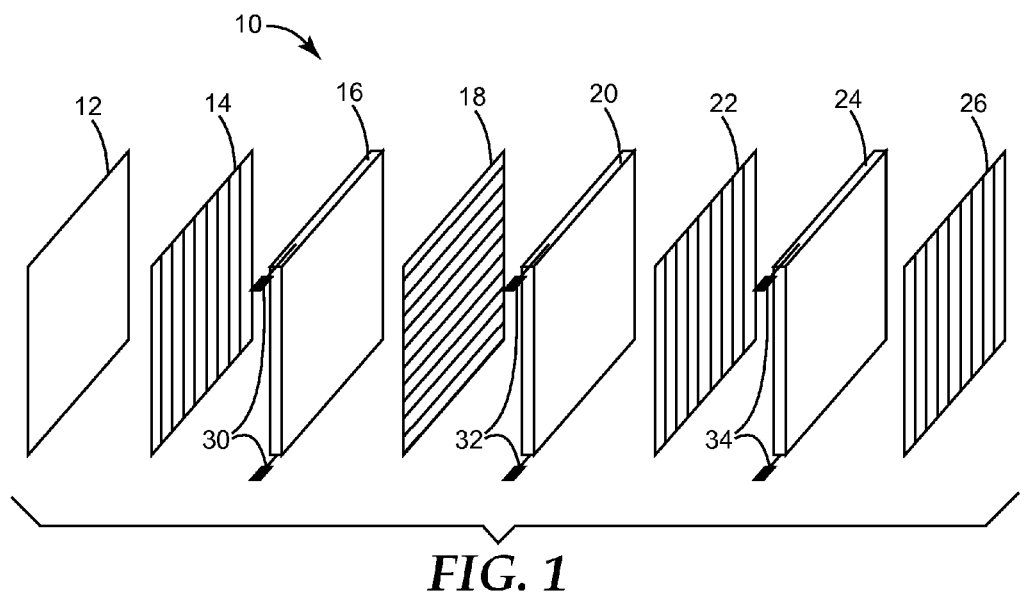
FIG. 1 is an exploded view of an automatic welding filter 10 according to the present invention.

FIG. 1 shows an exploded view of an automatic welding filter 10 according to the present invention. The outermost component of the welding filter 10 is a band pass filter 12 which serves to attenuate the IR and UV wavelength components from the high intensity welding light. This can be achieved using an interference filter which reflects IR radiation and absorbs the UVA, UVB and UVC components of the welding light. Alternatively, the skilled person will appreciate that band pass filter 12 could be achieved using a combination of separate IR and UV reflecting and/or absorbing filters. The function of the band pass filter 12 is to eliminate the hazardous IR and UV wavelength components from the high intensity welding light.

The automatic welding filter 10 also includes a first polarisation filter 14, a first optically rotating liquid crystal cell 16, a second polarisation filter 18, a second optically rotating liquid crystal cell 20, and a third polarisation filter 22. Polarisation filters 14, 18 and 22 have substantially orthogonal polarisation directions. In other words, the polarization direction of the second polarisation filter 18 is substantially orthogonal to the polarization direction of the first polarisation filter 14, and the third polarisation filter 22 has substantially the same polarisation direction as the first polarisation filter 14.

In optical alignment with these components is a colour-tunable filter whose spectral transmittance can be varied by a user to control and optimise the visual appearance of the welding task. The colour-tunable filter comprises a low twist liquid crystal cell 24 disposed between a pair of polarisation filters, the third polarisation filter 22 and a fourth polarisation filter 26. The polarisation filters 22 and 26 having substantially parallel polarisation directions. FIG. 1 also shows that each of the liquid crystal cells 16, 20 and 24 are provided with connectors 30, 32 and 34, respectively, by which control voltages can be applied.

The colour-tunable filter comprises a low twist liquid crystal cell 24 disposed between the third and fourth polarisation filters 22 and 26 having substantially parallel polarisation directions. As used in this document, the term "low twist" means having a twist angle of less than 90 degrees. For example, the low twist liquid crystal cell 24 has a twist angle of less than 90 degrees, typically zero or 1 to 60 degrees. More specifically, the twist angle of the low twist liquid crystal cell 24 is 30 to 50 degrees. The low twist colour-tunable liquid crystal cell 24 is in many ways similar in design as the low twist liquid crystal cells 16 and 20 described below, but its operation is totally different because it is sandwiched between parallel polarisers 22 and 26, as opposed to crossed polarisers. The colour-tunable liquid crystal cell 24 is dark and exhibits a certain colour, which appears predominately blue to the user, with no voltage is applied to the connectors 34. The colour-tunable liquid crystal cell 24 becomes optically transparent when a voltage greater than around 4.0V is applied. The viewed colour can then be varied at lower voltages (between around 0 and 2.0V), as described further in relation to FIG. 5. The skilled person will appreciate that the voltage levels will be different for varying cell designs, depending on the liquid crystal materials used, different cell gap geometries etc.

When using automatic welding filter 10, a user can select a number of pre-defined user colour and shade settings or levels. These can be inputted digitally or via, for example, via a dial or variable potentiometer or the like. The user-selected colour signal is then a voltage that is applied to the connectors 34 of the liquid crystal cell 24 and which alters the birefringence properties of the low twist liquid crystal cell 24. The optical effect is wavelength dependent and transmittance peaks occur for certain wavelengths. The transmittance peaks, i.e. a greater fraction of the incident light that is able to pass through the liquid crystal cell 24 at a specified wavelength, can be shifted to different wavelengths by varying the voltage, as described below.

Liquid crystal cells 16 and 20 are also "low twist" cells. That is, they have a twist angle of less than 90 degrees, typically zero or 1 to 89 degrees. A typical construction for this type of low twist cell consists of a twisted nematic type of liquid crystal material positioned between glass plates. The inwardly facing glass plates of the liquid crystal cells are provided with transparent electrically conductive electrode layers (e.g., indium tin oxide layers) on which there is applied, for instance, a polyimide layer that has been treated mechanically, such as by brushing or rubbing, in specific alignment directions. The resulting structure in the liquid crystal defining surfaces, forces the nematic molecules to take specific angular positions so that the molecules are twisted through their respective twist angle between the defining surfaces. In use, the low twist liquid crystal cell 24 is disposed between polarisation filters having substantially parallel polarisation directions that are aligned at an angle between 0 degrees and 15 degrees. In an electrically non-activated state (with no voltage applied to connectors 30 and 32), the polarisation plane is rotated as light passes through the cell and the filter becomes transparent. The orientation of the nematic liquid crystal molecules can be controlled by applying an electric field between the defining surfaces. In use, the twist angles of the first and second liquid crystal cells 16 and 20 are between 20 degrees and 85 degrees.

The application of a voltage to connectors 30 and 32 creates an electric field between the defining surfaces. The nematic liquid crystal molecules align with the electric field perpendicular to the defining surfaces, rather than parallel to them, and the cell achieves a darkened state. Thus, when a control voltage is applied to the low twist cells 16 and 20, a filter effect is obtained. The degree of rotation of the nematic molecules may be controlled by varying the control voltage, and thus the corresponding filter effect may also be controlled. The result is that liquid crystal cells 16 and 20 are in a light transmission state in the absence of an applied voltage, and in a dark transmission state in the presence of an applied voltage. The skilled person will appreciate that the voltage levels will be different for varying cell designs, depending on the liquid crystal materials used, different cell gap geometries etc. In use, the light transmission state corresponds to any of welding shades 2 to 4 and the dark transmission state, being user-selectable, corresponds to any of welding shades 7 to 14, defined according to EN 379:2003.

Figure 2:
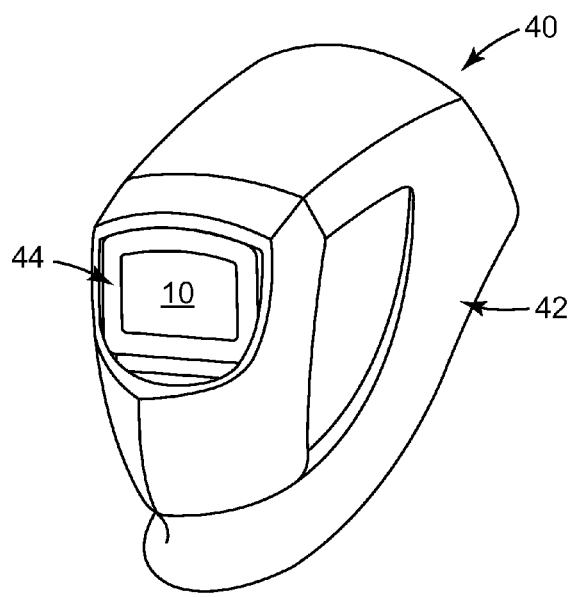
FIG. 2 is a perspective view of one embodiment of an automatic welding filter 10 of the present invention, mounted on a protective shield 40.

FIG. 2 is a perspective view of one embodiment of an automatic welding filter 10 of the present invention, mounted in an automatic darkening filter apparatus 44 that can be included in protective headgear, for example shield 40 (e.g. safety shield, also known as helmet). Shield 40 includes a shield body 42. Automatic darkening filter apparatus 44 includes automatic welding filter 10 that is placed in position to intercept electromagnetic radiation (e.g., visible light, UV light, IR, etc.). In a preferred embodiment, the automatic darkening filter apparatus 44 is positioned in shield body 42 so that it is directly in front of the wearer's eyes when the shield is worn by the user.

In other embodiments of the invention, one or more automatic darkening filter apparatuses 44 may be provided in any other suitable equipment or articles and for other applications. For example, automatic darkening filter apparatus 44 may be supplied as part of protective eyewear (e.g. goggles) rather than the full-coverage shield 42 of FIG. 2. Alternatively, automatic darkening filter apparatus 44 may be provided in a hand held device, or in a window or aperture allowing inspection of a room, enclosure, machinery space etc., in which high intensity light may be present.

Automatic darkening filter apparatus 44 can be used in connection with industrial operations, for example welding (e.g. arc welding, torch welding, acetylene welding), cutting (e.g. laser cutting, acetylene cutting), brazing, soldering and the like. It can also be used in connection with medical procedures involving high intensity light (e.g. laser surgery, hair removal, tattoo removal, light-curing of dental resins, etc.). The skilled person will appreciate that many other uses are possible.

Figure 3:
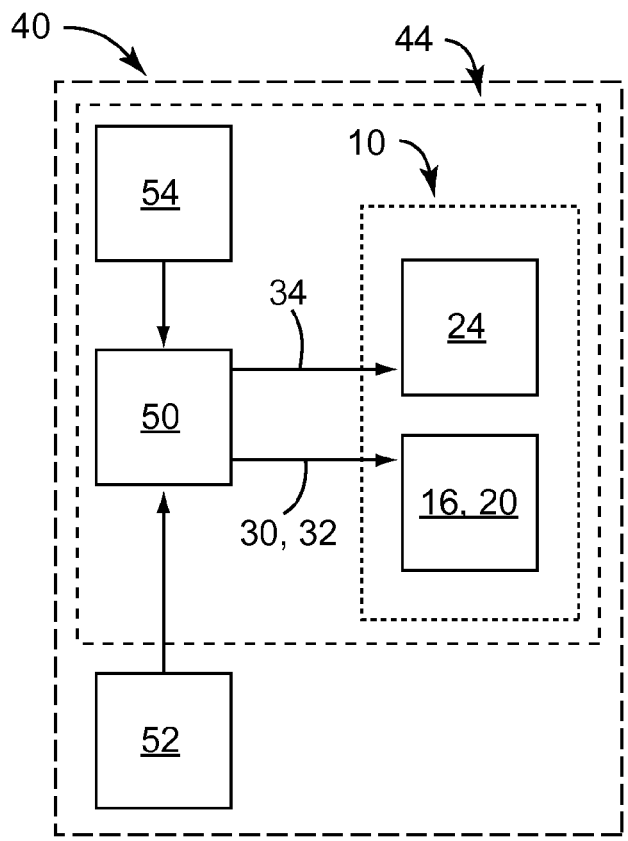
FIG. 3 is a block diagram which illustrates schematically the operation of an automatic welding filter 10 according to the present invention.

FIG. 3 is a block diagram which illustrates schematically the operation of an automatic welding filter 10 according to the present invention, and mounted in a protective shield 40. The automatic darkening filter apparatus 44 includes an electronic control unit 50 for receiving and controlling the various signals to the automatic welding filter 10 and, more particularly, liquid crystal cells 16, 20 and 24, via connectors 30, 32 and 34, respectively, as shown in FIG. 1.

The electronic control unit 50 receives two sets of user-selected signals, via a user input module 54. Firstly, the user can control the dark transmission state of the filter 10 between any of welding shades 7 to 14. Secondly, the user can independently select a number of pre-defined user colour settings which alter the colour of the automatic welding filter 10 inside the visible light spectrum of 380 nm to 780 nm. The pre-defined user colour settings can be inputted via digital means, i.e. specific inputs or buttons corresponding to red, green, or blue etc. Alternatively, the user-selected colour settings can be varied in a continuous or analogue manner, via a dial or variable potentiometer or the like, to optimise the visual appearance of a welding task.

The user is then able to adjust the colour of the automatic welding filter 10 in the dark transmission state, independently of the shade, to improve the visibility for a wide variety of welding tasks.

The electronic control unit 50 also includes an input detector 52. Detector 52 is capable of detecting at least an input that indicates the presence of high intensity welding light. In various embodiments, detector 52 may be located physically close to some or all of the other components (hardware, etc.) of automatic darkening filter apparatus 44 or may be located physically remote from some or all of the other components. In FIG. 3, the detector 52 is shown being physically located on the protective shield 40 but the skilled person will appreciate that the detector 52 could form part of the automatic darkening filter apparatus 44 or the welding filter 10 or be physically remote. The skilled person will appreciate that detector 52 can be implemented using various photodetector devices and technologies. Alternatively, the skilled person will appreciate that an input that indicates the presence of high intensity welding light can be generated by electronic control unit 50 in response to an activation signal generated by, for example, a welding tool or torch. This is set out in WO2007/047264 (Garbergs, et al.), and such an approach may also be used in connection with the present invention.

In the event of failure of the electronic control unit 50, the colour-tunable filter 24 defaults to a fail-safe mode of operation by providing an intermediate transmission state. The intermediate transmission state is a fail-safe or power-off mode that corresponds to any of welding shades 5 to 8, defined according to EN 379:2003.

Figure 4:
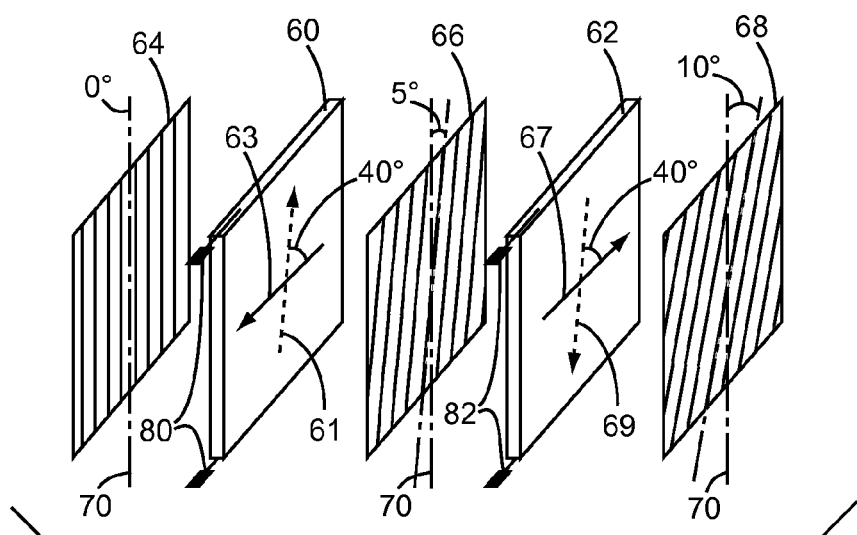
FIG. 4 is an exploded view of a colour-tunable filter according to the present invention.

Whilst FIG. 1 illustrates a preferred embodiment of the colour-tunable filter as being a single low twist liquid crystal cell 24 disposed between substantially parallel polarizers 22 and 26, a further embodiment of the invention is illustrated in FIG. 4.

FIG. 4 shows an exploded view of a colour-tunable filter that comprises two liquid crystal cells 60 and 62 that are disposed between polarisation filters 64, 66 and 68. The first liquid crystal cell 60 is disposed between first and second polarisation filters 64 and 66, and wherein the second liquid crystal cell 62 is disposed between second and third polarisation filters 66 and 68. The twist angle of the liquid crystal molecules in the two liquid crystal cells 60 and 62 is 40 degrees. The two liquid crystal cells 60 and 62 are substantially identical, but they are rotated by 180 degrees with respect to each other, to give less colour variation for different viewing angles.

The liquid crystals used are of the nematic type with a Δn (difference between the refractive index of ordinary and extraordinary light rays) of 0.09 sandwiched between two optically clear substrates having a cell gap of 4 μm. The inwardly facing surfaces of the optically clear substrates of the liquid crystal cells 60 and 62 are provided with transparent conductive electrode layers (e.g., indium tin oxide layers) on which there is applied an alignment layer, for instance a polyimide layer that has been treated mechanically, such as by brushing or rubbing, in specific alignment directions. The resulting structure in the liquid crystal defining surfaces, forces the nematic molecules to take specific angular positions so that the molecules are twisted through their respective twist angle between the defining surfaces.

The application of a voltage to connectors 80 and 82 creates an electric field between the liquid crystal defining surfaces. The nematic liquid crystal molecules align with the electric field perpendicular to the defining surfaces, rather than parallel to them, and the cells exhibits different spectral transmittance responses.

In the embodiment shown in FIG. 4, the alignment directions of the liquid crystal cells 60 and 62 are arranged substantially parallel to and oriented asymmetrically with respect to one another. For example, the alignment direction 61 of liquid crystal cell 60 is arranged substantially parallel to and oriented asymmetrically (i.e. in an opposite direction) with respect to alignment direction 69 of liquid crystal cell 62. Similarly, alignment direction 63 of liquid crystal cell 60 is arranged substantially parallel to and oriented asymmetrically with respect to alignment direction 67 of liquid crystal cell 62. This asymmetric orientation is illustrated by the opposite pointing arrows indicating the alignment directions 61, 63 and 67, 69 in FIG. 4.

The polarisers 64, 66 and 68 have different orientations, 0 degrees, 5 degrees and 10 degrees respectively from the vertical axis 70. The polariser orientations have been selected to give a suitable spectral transmittance (colour) without voltage applied to connectors 80 and 82 and to minimise variations in colour over the viewing area of the welding filter 10 caused by cell gap variations.

Figure 5:
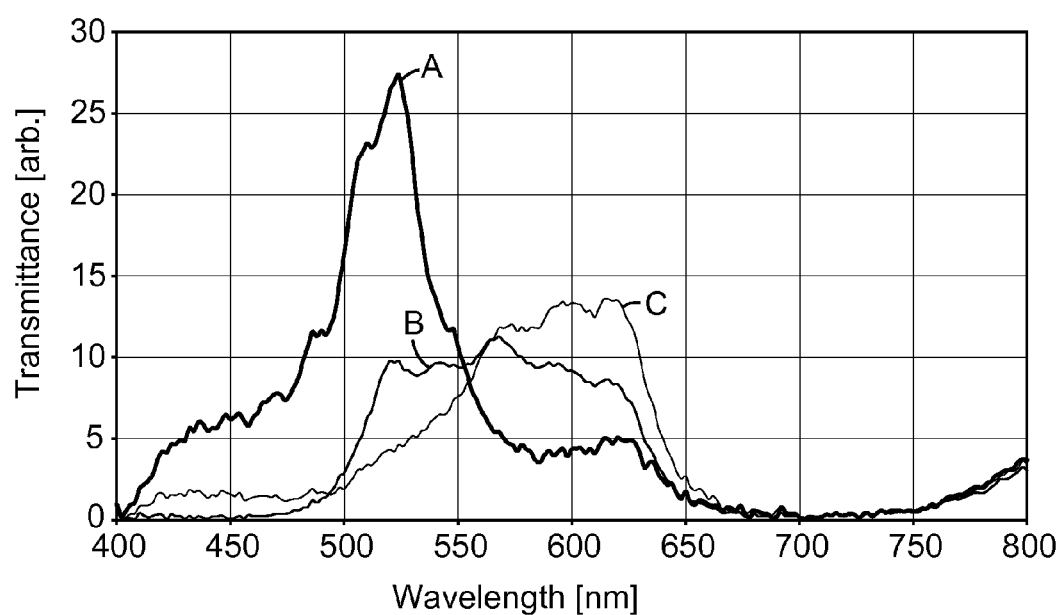
FIG. 5 shows the spectral transmittance responses obtained from the automatic welding filter 10 of the present invention as the user-selected colour signal is varied.

FIG. 5 shows different spectral transmittance responses obtained from the automatic welding filter 10 illustrated in FIG. 1. FIG. 5 shows three different spectral transmittance curves obtained for an automatic welding filter of the present invention. The different spectral transmittance responses exhibit different colours at the same welding shade, defined according to EN 379:2003.

Spectral response A is obtained when no voltage (0V) is applied to the colour-tunable filter. The colour that is observed through the automatic welding filter appears blue. Spectral response B is obtained by applying a voltage of around 1.6V to the colour-tunable filter. The colour that is observed through the automatic welding filter appears green. Spectral response C is obtained by applying a voltage of around 1.3V to the colour-tunable filter. The colour that is observed through the automatic welding filter appears red. This order is due to that there are two transmittance peaks. The blue transmittance peak disappears when voltage is applied and the peak coming from the red side is moving towards the shorter wavelengths as the voltage is increased.

As mentioned, the user can select a number of pre-defined user colour settings which alter the colour of the automatic welding filter 10 inside the visible light spectrum of 380 nm to 780 nm. The pre-defined user colour settings can be inputted digitally or via, for example, a dial or variable potentiometer. When no voltage signal is applied to the colour-tunable filter, the spectral transmission curve has a peak in the shorter wavelength part of the visible light spectrum and the view through the automatic welding filter 10 is predominantly blue. As the voltage is increased the spectral transmission curve is shifted towards shorter wavelengths. The blue transmittance peak moves away from the visible range and another transmittance peak moves into the visible range from the infrared side. In a high voltage condition, the colour-tunable filter is shifted to a transparent colour which is mainly used when the automatic welding filter 10 is in the light transmission state.

The invention claimed is:

1. An automatic welding filter, comprising:
   a switchable filter that changes from a light transmission state to a dark transmission state in response to an activation signal;
   a colour-tunable filter, being in optical alignment with the switchable filter, whose spectral transmittance is adapted to vary in response to a user-selected colour signal; and
   an electronic control unit for receiving and controlling the signals.

2. The automatic welding filter of claim 1, wherein the colour-tunable filter comprises at least one low twist liquid crystal cell disposed between polarisation filters having substantially parallel polarisation directions.

3. The automatic welding filter of claim 2, wherein the user-selected colour signal alters the birefringence properties of the low twist liquid crystal cell.

4. The automatic welding filter of claim 2, wherein the twist angle of the low twist liquid crystal cell is between 0 degrees and 60 degrees.

5. The automatic welding filter of claim 2, wherein the twist angle of the low twist liquid crystal cell is between 30 degrees and 50 degrees.

6. The automatic welding filter of claim 2, wherein the polarisation filters having substantially parallel polarisation directions are aligned at an angle between 0 degrees and 15 degrees.

7. The automatic welding filter of claim 1, wherein the switchable filter comprises first and second twisted nematic liquid crystal cells; and wherein the first liquid crystal cell is disposed between first and second polarisation filters, and wherein the second liquid crystal cell is disposed between second and third polarisation filters, the polarisation filters having substantially orthogonal polarisation directions; and a band pass filter.

8. The automatic welding filter of claim 7, wherein the twist angles of the first and second liquid crystal cells are between 20 degrees and 85 degrees.

9. The automatic welding filter of claim 7, wherein the bass pass filter attenuates the IR and UV wavelength 5 components.

10. The automatic welding filter of claim 1, wherein in the event of failure of the electronic control unit the colour-tunable filter defaults to a fail-safe mode of operation by providing an intermediate transmission state.

11. The automatic welding filter of claim 1, wherein the light transmission state corresponds to any of welding shades 2 to 4 and the dark transmission state corresponds to any of welding shades 7 to 14.

12. The automatic welding filter of claim 10, wherein the intermediate transmission state corresponds to any of welding shades 5 to 8.

13. The automatic welding filter of claim 1, wherein the user-selected colour signal is independent of the transmission state of the switchable filter.

14. The automatic welding filter of claim 1, wherein the user-selected colour signal is adapted to vary in a continuous manner or by selecting a plurality of pre-defined user settings.

15. The automatic welding filter of claim 1, wherein the spectral transmittance of the colour-tunable filter can be varied in the visible light range of 380 nm to 780 nm.

16. A welding shield, comprising:
   a protective shell with the automatic welding filter of claim 1 disposed therein; and
   at least one sensor connected to the electronic control unit to detect incident light, the electronic control unit causes a voltage to be applied to the switchable filter in response to the activation signal which is indicative of the presence of incident light.

17. The welding shield of claim 16, wherein the automatic welding filter is replaceable.

18. A method of filtering high intensity welding light, comprising the steps of:
   directing the light through a band pass filter that attenuates the IR and UV wavelength components;
   directing the light through a switchable filter that automatically changes from a light transmission state to a dark transmission state in response to an activation signal; and
   directing the light through a colour-tunable filter whose spectral transmittance can be varied in response to a user-selected colour signal.

19. The method of claim 18, wherein the switchable filter and colour-tunable filters are liquid crystal cells.

20. The method of claim 18, further comprising the steps of:
   detecting the presence of high intensity welding light using at least one sensor connected to an electronic control unit; and
   applying a voltage to the switchable filter in response to the sensed activation signal.

* * * * *